US012569465B2

(12) United States Patent
Ma et al.

(10) Patent No.: US 12,569,465 B2
(45) Date of Patent: Mar. 10, 2026

(54) METHOD FOR ACTIVATING FOLLICLES BY MEANS OF USING SMALL-MOLECULE COMPOUND, AND PREPARATION THEREOF

(71) Applicants: TSINGTAO A-SMART MEDICAL TECHNOLOGY CO., LTD., Shandong (CN); SHANDONG UNIVERSITY, Shandong (CN)

(72) Inventors: Jinlong Ma, Shandong (CN); Hongbin Liu, Shandong (CN); Lianbao Cao, Shandong (CN); Keliang Wu, Shandong (CN); Xianwei Su, Shandong (CN); Gang Lu, Shandong (CN)

(73) Assignees: TSINGTAO A-SMART MEDICAL TECHNOLOGY CO., LTD., Shandong (CN); SHANDONG UNIVERSITY, Shandong (CN)

( * ) Notice: Subject to any disclaimer, the term of this patent is extended or adjusted under 35 U.S.C. 154(b) by 565 days.

(21) Appl. No.: 18/005,035

(22) PCT Filed: Jul. 8, 2021

(86) PCT No.: PCT/CN2021/105248

§ 371 (c)(1),
(2) Date: Jan. 10, 2023

(87) PCT Pub. No.: WO2022/007897

PCT Pub. Date: Jan. 13, 2022

(65) Prior Publication Data

US 2023/0330055 A1 Oct. 19, 2023

(30) Foreign Application Priority Data

Jul. 10, 2020 (CN) ........................ 202010662524.2

(51) Int. Cl.
*A61K 31/336* (2006.01)
*A61P 15/08* (2006.01)
*C12N 5/071* (2010.01)

(52) U.S. Cl.
CPC ............ *A61K 31/336* (2013.01); *A61P 15/08* (2018.01); *C12N 5/0682* (2013.01); *C12N 2500/30* (2013.01)

(58) Field of Classification Search
CPC ........ A61K 31/336; A61K 31/33; A61P 15/08
See application file for complete search history.

(56) References Cited

U.S. PATENT DOCUMENTS

2014/0249364 A1 9/2014 Bukovsky et al.
2019/0177689 A1 6/2019 Baharvand et al.

FOREIGN PATENT DOCUMENTS

WO 2009027551 A1 3/2009
WO 2020088180 A1 5/2020

OTHER PUBLICATIONS

Hoyer et al., Toxicologic Pathology, vol. 29, No. 1, pp. 91-99, 2001 (Year: 2001).*

(Continued)

*Primary Examiner* — San Ming R Hui
(74) *Attorney, Agent, or Firm* — Kim IP Law Group LLC

(57) ABSTRACT

Disclosed are a method and culture medium for performing an in vivo treatment on ovaries of mammals including humans or performing in vitro culturing on ex vivo ovaries or ovarian tissue by means of using 4-vinylcyclohexene diepoxide. The method or culture medium provided facilitates the retention and enhancement of the developmental and reproductive potential of mammalian ovaries or ovarian tissue, and is particularly capable of promoting follicle maturation and increasing the number of ovulations.

5 Claims, 4 Drawing Sheets

(56) References Cited

OTHER PUBLICATIONS

Kappeler et al., Systems Biology in Reproductive Medicine, 2012, 58: 57-62 (Year: 2012).*
Appt et al., "Destruction of primordial ovarian follicles in adult cynomolgus macaques after exposure to 4-vinylcyclohexene diepoxide: a nonhuman primate model of the menopausal transition", Fertility and Sterility, vol. 86, Suppl 3, pp. 1210-1216, Oct. 2006.
Devine et al., "Characterization of a Rat in Vitro Ovarian Culture System to Study the Ovarian Toxicant 4-Vinylcyclohexene Diepoxide", Toxicology and Applied Pharmacology, 184, 107-115, 2002. doi: 10.1006/taap.2002.9502.
Borman et al., "A Single Dose of the Ovotoxicant 4-Vinylcyclohexene Diepoxide Is Protective in Rat Primary Ovarian Follicles", Toxicology and Applied Pharmacology 158, 244-252, 1999.
Cao Lianbao et al. "Hormone-Like Effects of 4-Vinylcyclohexene Diepoxide on Follicular Development" Frontiers in Cell and Developmental Biology, vol. 8, No. 587, Jul. 31, 2020, pp. 1-15.
International Search Report mailed Oct. 9, 2021 in International Application No. PCT/CN2021/105248.
Written Opinion mailed Oct. 9, 2021 in International Application No. PCT/CN2021/105248.

* cited by examiner

*Note:1: control;2: 1nM; 3: 10nM; 4:100nM; 5: 1000nM; 6: FSH*

METHOD FOR ACTIVATING FOLLICLES BY MEANS OF USING SMALL-MOLECULE COMPOUND, AND PREPARATION THEREOF

The present application claims priority to Chinese Patent Application No. 202010662524.2 with a title of "Method for activation follicles by means of using small-molecule compound, and preparation thereof" and filed on Jul. 10, 2020. The disclosure of above application is hereby incorporated into the present application by reference in their entirety.

FIELD OF THE INVENTION

The present invention relates to the reproductive field of mammals including humans. Specifically, the present invention relates to a method for improving the developmental ability of ovaries or ovarian tissues in mammals including humans, and an in vitro cultivation method and culture medium for ovaries or ovarian tissues.

BACKGROUND

The number of follicles contained in the ovaries of female mammals has been determined at birth. As the age increases, a large part of follicles will go to apoptotic atresia during ovarian development, and only a few follicles will eventually undergo the whole process of primordial follicle, primary follicle, secondary follicle, preovulatory follicle, ovulation, finally matures and is released. As mammals age, the functional ovarian reserve (FOR) and maturation capacity decline, and in some cases, it is difficult to continue growing to maturity even if primary follicles or small secondary follicles are present. At the same time, with the increase of age, the body's ability to respond to endogenous or exogenous hormones such as follicle-stimulating hormone (FSH) also decreases.

Oocytes maturation is crucial in human reproduction, including the field of assisted reproduction, and also plays an important role in the development of animal husbandry. In human females, women of advanced reproductive age have reduced ovarian reserve, which is insufficient for a successful pregnancy. In addition, it is difficult for some patients who need assisted reproduction to meet their fertility requirements to obtain enough high-quality eggs from the ovaries. Clinically, some patients, such as patients who need radiation therapy, will have part of their ovarian tissue removed and preserved for possible future reproductive use. In animal husbandry, the continuation of the genes of livestock with good genes is particularly important. Even in the stages of old age and declining fertility, there is still a need to reproduce offspring. In these cases, the protection of the ovary as well as the maintenance and promotion of its follicular developmental potential are extremely important.

4-Vinylcyclohexene diepoxide (VCD) is an intermediate used in the manufacture of flame retardants, flavors, pesticides, adhesives, fragrances, and synthetic rubber. It has been found to pose a threat to the development of follicles in the ovary of mammals. Prior studies consistently indicated that VCD induces atretic degeneration of primordial and primary follicles in rodents. Such VCD-induced ovotoxicity has been associated with the B-cell lymphoma 2 (Bcl-2) pro-apoptotic signaling pathway, with kit ligand (KIT/KTL) signaling, and with the nuclear factor erythroid 2-related factor 2 (Nrf2)-mediated oxidative stress response pathway. As a research compound, VCD is commonly used to chemically induce animal models of premature ovarian insufficiency (POI), one of the common causes of female infertility; VCD depletes FOR, enabling the study of the etiopathogenesis of this reproductive disorder.

In the field of assisted reproduction in mammals, including humans, more research is needed on the development of the ovary, and there is a need for methods that are beneficial to the development of the ovary, especially to maintain and improve the potential and ability of blastocysts in the ovary to transform into oocytes, and a medium that can be used to culture ovaries or ovarian tissues in vitro.

SUMMARY OF THE INVENTION

The present invention discovers and proves for the first time that low-concentration and/or short-time 4-vinylcyclohexene diepoxide (VCD) treatment has a hormone-like effect on ovary or cultured ovary tissue, which is beneficial to the development of ovary of female mammals and the maintenance and even enhancement of reproductive potential, especially the development of early follicles and the further maturation of secondary follicles to the final ovulatory state. The present invention thus provides a method and a culture medium for treating mammalian ovaries including human ovaries in vivo, or culturing isolated ovaries or ovarian tissues in vitro with 4-vinylcyclohexene diepoxide.

Specifically, the present invention provides a medium for culturing mammalian ovaries or ovarian tissues, the medium comprising 4-vinylcyclohexene diepoxide. In one aspect of the present invention, the content (concentration) of 4-vinylcyclohexene diepoxide in the medium is about 0.1 nM-5000 nM, preferably about 1 nM-1000 nM, more preferably about 1 nM-20 nM. In one aspect of the present invention, the content of 4-vinylcyclohexene diepoxide in the medium is less than 1000 nM.

4-vinylcyclohexene diepoxide (VCD), has a structure as shown below:

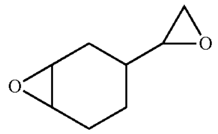

In the present invention, the mammals can be any kind of Mammalian animals, including but not limited to rodentia (such as mice and rats), lagomorpha (rabbits), carnivora (felines and canines)), artiodactyla (bovines and porcines), persistodactyla (equines), or primates and apes (humans or monkeys). The mammals are preferably humans or mice.

In the present invention, the ovary or ovarian tissue used for culture may be a whole ovary or a part of an ovary, or a tissue of the ovary, such as ovarian cortical tissue. The ovary or ovarian tissue can be an isolated ovary or a part thereof, or an isolated ovarian tissue of an animal. It can also be an ovary or ovarian tissue recovered after cryopreservation, or it can be an ovary or ovarian tissue cultured in cell culture or culture medium. In the present invention, the ovary or ovarian tissue contains follicles of different developmental stages. The purpose of the culture medium and culture method provided by the present invention is to maintain/stimulate the activity, developmental potential and ovulation of follicles in the ovary or ovarian tissue of a mammal.

In one aspect of the present invention, the content of 4-vinylcyclohexene diepoxide refers to the working concentration, that is, the concentration in the organ/tissue culture environment. In some cases, 4-vinylcyclohexene diepoxide of the present invention is provided in multiples of the working concentration. For example, in order to facilitate storage or operation, the components of the culture medium are provided at 5 times or 10 times the working concentration, and water/solution/culture solution are added for dilution when used.

The medium provided by the invention also contains one or more of the following other compounds: inorganic salts, energy sources, amino acids, proteins, cytokines, chelating agents, antibiotics, hyaluronic acid, growth factors, hormones or vitamins.

In one aspect of the invention, the inorganic salt may be an inorganic salt that dissociates into inorganic ions in an aqueous solution. Suitably, the inorganic salt may be an inorganic salt comprising one or more of the following inorganic ions: $Na^+$, $K^+$, $Cl^-$, $Ca^{2+}$, $Mg^{2+}$, $SO_4^{2-}$, or $PO_4^{3-}$.

In one aspect of the invention, the energy source may be pyruvic acid, lactic acid or glucose and the like.

In one aspect of the invention, the protein source can be albumin or synthetic serum. Suitable sources for protein supplementation include human serum, human cord serum (HCS), human serum albumin (HSA), fetal calf serum (FCS) or bovine serum albumin (BSA).

In one aspect of the invention, the one or more additional compounds may be a buffered solution. Suitable buffer solutions include, for example, HEPES buffer or MOPS buffer.

In one aspect of the invention, the one or more additional compounds may be background medium. That is, the culture medium provided by the present invention adds 4-vinylcyclohexene diepoxide in the background culture medium. Background culture medium can be available medium suitable for culturing organs or tissues, such as commercially available minimal medium, simple medium or supplemented medium.

In another aspect of the present invention, the present invention provides a method for culturing mammalian ovaries or ovarian tissues in vitro, wherein 4-vinylcyclohexene diepoxide is added to the medium. In still another aspect of the present invention, the content of 4-vinylcyclohexene diepoxide added is about 0.1 nM-5000 nM, preferably about 1-1000 nM, more preferably about 1-20 nM. In one aspect of the present invention, the content of 4-vinylcyclohexene diepoxide added is less than 1000 nM.

In one aspect of the present invention, in the above-mentioned in vitro culture method, the time for the ovary or ovarian tissue being cultured in the culture medium with 4-vinylcyclohexene diepoxide is no more than 6 days, preferably no more than 4 days, most preferably no more than 1 day.

In one aspect of the invention, the above in vitro culture method is used to treat ovary or ovarian tissue of juvenile or young mammals. In still another aspect of the present invention, the time for the ovary or ovarian tissue being cultured in the culture medium with 4-vinylcyclohexene diepoxide is no more than 4 days, most preferably no more than 1 day.

In one aspect of the present invention, the above-mentioned in vitro culture method is used to treat ovary or ovarian tissue of middle-aged or old mammals. In yet another aspect of the present invention, the time for the ovary or ovarian tissue being cultured in the culture medium with 4-vinylcyclohexene diepoxide is no more than 6 days, most preferably no more than 4 days.

In the present invention, "juvenile", "young", "middle-aged", and "old" of a mammal are defined from the perspective of the life cycle of the mammal. In one aspect of the invention, the life cycle is closely related to the reproductive cycle of mammals. "Juvenile" and "young" generally refer to a mammal in an age before normal reproductive age or within normal reproductive age (especially early normal reproductive age). "Middle age" and "old" generally refer to a mammal in an age late or after the normal reproductive age.

In another aspect of the present invention, the present invention provides a method of improving ovarian function in a mammal, wherein 4-vinylcyclohexene diepoxide is administered to the ovary of the mammal. In yet another aspect of the present invention, about 5-200 mg/kg body weight, preferably about 10-160 mg/kg body weight, more preferably about 20-100 mg/kg body weight of 4-vinylcyclohexyl diepoxide is administered to the ovary of the mammal.

In one aspect of the present invention, the above method stimulates the maturation of follicles in the mammal, including but not limited to stimulating the activation of primordial follicles, stimulating the transformation of primordial follicles into primary follicles, or stimulating the transformation of primary follicles into secondary follicles.

In one aspect of the invention, the above method stimulates ovulation in said mammal, ie increases the number of mature oocytes released.

In one aspect of the present invention, in the above method, 4-vinylcyclohexene diepoxide is administered to said mammal at intervals. In one embodiment, 4-vinylcyclohexene diepoxide is administered at intervals of about 12-48 hours, preferably at intervals of about 20-24 hours.

In one aspect of the invention, in the above method, 4-vinylcyclohexene diepoxide is administered to said mammal for a short period of time. In one of the embodiments, 4-vinylcyclohexene diepoxide is administered to said mammal not more than 10 days, preferably not more than 5 days, most preferably not more than 3 days.

The method of the present invention is suitable for exert the effects of 4-vinylcyclohexene diepoxide on the ovary. In one aspect of the present invention, in the above method, 4-vinylcyclohexene diepoxide is administered intraperitoneally.

In one aspect of the present invention, the above method is used to treat patients whose ovaries have been removed clinically, for example, patients whose ovaries have been partially or completely removed for ex vivo preservation due to the need for radiotherapy.

In one aspect of the present invention, the above method is used for the treatment of ovarian-related reproductive disorders in mammals, especially humans, especially reproductive disorders due to reduced number or decreased activity of follicles in the ovary, such as premature ovarian failure (POI) or ovarian reserve decreased function (DOR), etc. In yet another aspect of the present invention, the above method is used in the field of human assisted reproduction.

In one aspect of the present invention, use of 4-vinylcyclohexene diepoxide in the preparation of a medicament for improving ovarian function in mammals is provided.

In yet another aspect of the present invention, 4-vinylcyclohexene diepoxide is formulated to be administered to the mammal at a dosage of about 5-200 mg/kg body weight, preferably 10-160 mg/kg body weight, more preferably 20-100 mg/kg body weight.

In one aspect of the present invention, in the above use, the medicament is of a dosage form of multiple administrations. In one of the embodiments, the medicament is formulated as a dosage form that is administered at an interval of about 12-48 hours, preferably a dosage form that is administered at an interval of about 20-24 hours.

In one aspect of the present invention, in the above use, the medicament is for short-term administration. In one of the embodiments, the medicament with 4-vinylcyclohexene diepoxide is administered for no more than 10 days, preferably no more than 5 days.

In one aspect of the present invention, the medicament is used to treat ovarian-related reproductive disorders in mammals, such as premature ovarian failure (PO) or decreased ovarian reserve (DOR).

In yet another aspect of the present invention, the medicament is a dosage form for intraperitoneal administration Without wishing to be bound by theory, applicants believe that the discovery of this invention, that is, low concentration and/or short duration treatment with 4-vinylcyclohexene diepoxide (VCD) is beneficial to the development of ovary of female mammals and the maintenance and even enhancement of reproductive potential, especially the development of early follicles and the further maturation of secondary follicles to the final ovulatory state, is due to that low concentration and/or short duration treatment with 4-vinylcyclohexene diepoxide has hormone-like effects on ovary or cultured ovarian tissue, and can transiently activate PI3K-akt and mTOR pathways; in addition, low concentration and/or short-term 4-vinylcyclohexene diepoxide treatment also increases expression of aromatase in ovarian granulosa cells stimulates estrogen production. The present invention thus provides a method and a culture medium for treating mammalian ovaries including human ovaries in vivo, or culturing isolated ovaries or ovarian tissues in vitro with 4-vinylcyclohexene diepoxide.

Herein, where a range of values is provided, it is understood that, unless the context clearly dictates otherwise, there is no difference between any stated or intervening value in that stated range and any other stated or intervening value in that stated range. Each smaller range is included in this disclosure. "About" herein means that the described numerical value includes normal fluctuations within the range understood by those skilled in the art. Generally, "about" means ±10%. In some instances, "about" means ±5%. In certain specific cases, "about" means ±1%.

BRIEF DESCRIPTION OF THE DRAWINGS

FIG. 1A shows the staining of ovarian sections from different treatment groups. FIG. 1B shows the results of counting follicles of all levels in ovarian tissues of different treatment groups. FIG. 1C shows Immunoblotting of phosphorylation levels for several proteins associated with follicle activation in ovaries.

FIG. 2A shows the staining of ovarian sections in different treatment groups. FIG. 2B shows the results of counting secondary follicles in ovarian tissues of different treatment groups.

FIG. 3A shows the staining of ovarian sections from different treatment groups. FIG. 3B shows the results of follicle counting in ovarian tissues of different treatment groups.

FIG. 4A shows the staining of ovarian sections from different treatment groups. FIG. 4B shows the results of counting different follicles in the ovarian tissue of different treatment groups. FIG. 4C shows the MII oocytes obtained by ovulation stimulation (arrows point to MII oocytes). FIG. 4D shows the results of MU oocytes counts in the experimental and control groups.

FIG. 5A-B shows that the expression level of aromatase in granulosa cells of mice was significantly increased after VCD treatment. FIG. 5C-D shows that the expression level of aromatase in KGN was significantly increased after VCD treatment.

DETAILED DESCRIPTION

Figure 1:
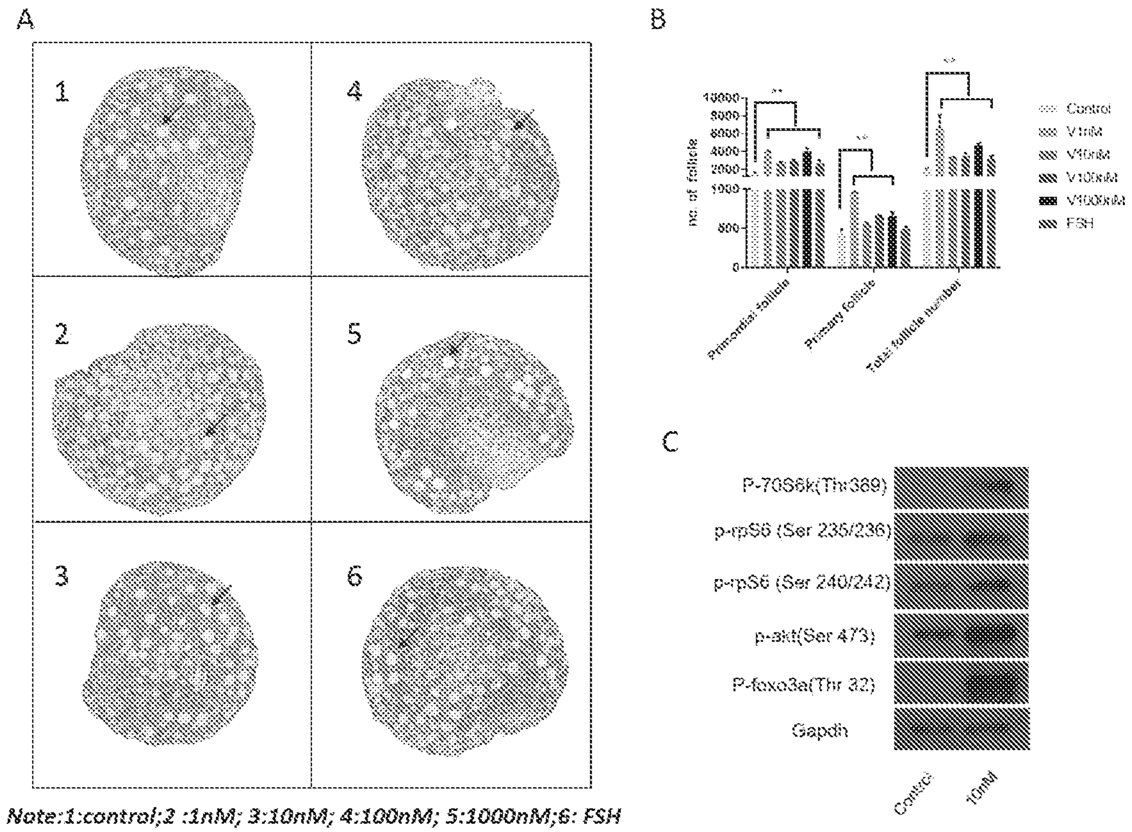
FIG. 1 shows that culturing with 4-vinylcyclohexene diepoxide (VCD) stimulates activation of primordial follicles in in vitro experiments.

The technical details and benefits of the invention provided in the present disclosure are further described in the following examples, which are intended to illustrate the inventions and not to limit the scope of the present disclosure.

Example 1 Experimental Method and Reagents 4-vinylcyclohexene diepoxide (VCD) was purchased from Sigma Aldrich (Cat #94956-100 ML). For in vitro maturation, and in vitro fertilization, VCD was dissolved in phosphate-buffered saline (PBS) (Cat #10010-0323, Gibco). For intraperitoneal injection, VCD was dissolved in saline (0.9% sodium chloride).

In Vitro Culture of Neonatal Mouse Ovary

Separating Mouse Ovary

Neonatal 2-day (PD2) or 12-day (PD12) C57bl/6 mice (provided by Shandong University Experimental Animal Center) were executed by decapitation and the ovaries and surrounding tissues were dissected and separated under a dissecting microscope, and the excised ovaries were placed in Leibovitz's L-15 medium (containing 10% fetal bovine serum+0.5% penicillin+0.5% streptomycin). The adipose tissue was dissected and separated. The separated ovaries were washed three times in PBS.

Culture of Mouse Ovary

Configure ovarian medium: 1 mg/ml bovine serum albumin (BSA, Cat #A4161-1G, Sigma), 1 mg/ml AbluMAX II Lipid-Rich BSA (Cat #11021029, Gibco), 5% Insulin-Transferrin-Selenium (ITS-G) (Cat #41400-045, Gibco), 0.5% Penicillin+0.5% Streptomycin and 100 nM VCD were added into DMEM/F12 (Cat #11039-021, Gibco) medium. The prepared medium was mixed and added to a six-well plate with 1.5 ml of medium per well. A sieve (Cat #PICMORG50, Millipore) was put on the medium and placed in the incubator to preheat.

The separated ovaries were transferred to the ovarian medium with a pipette, washed three times and placed on the upper sieve of the pre-warmed medium. A drop of medium was added around the ovaries in the upper sieve to keep the area around the ovaries moist. The six-well plates were placed in a 37° C., 5% CO2 incubator for four consecutive days, and the lower layer of medium was changed daily. For PD2 mice ovaries, VCD was added to the medium on the first day of incubation only. PD12 mice ovaries were continuously exposed to VCD for four days.

Neonatal Mice were Injected Intravenously and Ovarian Changes were Observed

PD12 C57bl/6 mice in the same litter were divided into experimental and control groups according to body weight. The experimental mice were weighed and given either 20 mg/kg or 160 mg/kg of VCD by intraperitoneal injection, while the control mice were given the same volume of saline. After ten days of continuous administration, the mice were executed and the ovaries were dissected to separate the adipose tissue under the microscope and fixed in 4% PFA. Dehydrated sections were used to observe and count the development of follicles in the ovaries at different times.

Ovulation Stimulation Experiment in Old Mice 10-12 month old C57bl/6 rats were divided into experimental and control groups according to body weight, and the experimental group was weighed and injected intraperitoneally with 80 mg/kg of VCD, while the control group was given the same volume of saline. After 5 days of continuous administration, 5 units of PMSG were injected to the experimental group and the control group, and 10 IU of hCG was injected 48 hours later to induce secondary ovulation. Mice were executed 16 hours after hCG injection, and both oviducts were collected and placed in M2 dissecting solution (Cat #M7167, Sigma), and the oocyte-granulosa cell complexes were seen when cutting the dilated oviducts under a dissecting microscope. The granulosa cell complexes from each mouse were transferred to a droplet of hyaluronidase (Cat #90101, Fujifilm Irvine Scientific) and the number of eggs per mouse was counted under a microscope after the granulosa cells around the oocytes had been digested.

Western Blot Assay for Phosphorylation of Proteins Associated with Follicle Activation in the Ovary PD2 mice were dissected in autopsy solution (Leibovitz's L-15 medium, Cat #41400-045, Gibco; +10% fetal bovine serum (FBS)) after execution, washed twice in ovarian medium and incubated in ovarian medium. After incubation in medium with or without VCD for 3 min. ovarian tissue was collected and lysed in RIPA lysis solution (Cat #89900, Thermo) for digestion. Proteins were denatured and separated by SDS PAGE and transferred to PVDF membranes (Millipore). The membranes were incubated with primary antibodies followed by incubation with HRP-conjugated secondary antibodies and the bands were examined using an enhanced chemiluminescence detection kit (Bio-Rad).

Antibody Information anti-rabbit aromatase (Cat #NBP1-45360, Novus, 1:2000), anti-rabbit phosphor-AKT (Serine 473) (D9E) (Cat #4060, Cell Signaling, 1:500), anti-rabbit phosphor-FoxO1 (Threonine 24)/FoxO3a (Threonine 32) (Cat #9464, Cell Signaling, 1:500), anti-rabbit phosphor-P-S6 (Serine 235/236) (Cat #4858, Cell Signaling, 1:1000), anti-rabbit phosphor-P-S6 (Serine 240/244) (Cat #2215, Cell Signaling, 1:1000), anti-rabbit phosphor-P70S6k (Threonine 389) (Cat #9205, Cell Signaling, 1:1000), anti-rabbit (Cat #7074S, CST) or anti-mouse (Cat #7076S, CST).

Detection of Estradiol (E2) Levels in Cell Culture Supernatants (ELISA)

KGN cell supernatants were collected after 24 hours of cell culture for the detection of E2 levels. The procedure of the assay followed the instructions of the E2 Assay Kit (Human Estradiol (E2) ELISA Kit, Cat #KAQ0621, Invitrogen).

Statistical Analysis

Data are expressed as the mean±standard deviation from at least three independent experiments. Statistical comparisons were performed using one-way ANOVA, and statistical differences were set at $P<0.05$.

Example 2 Short-Time VCD Culture Stimulates Activation of Primordial Follicles in an In Vitro Experiment The experimental procedure and results are shown in FIG. 1.

Two-day-old (PD2) mouse ovaries were isolated and cultured in vitro according to the method described in Example 1. Different concentrations of 4-vinylcyclohexene diepoxide (VCD) (0, 1 nM, 10 nM, 100 nM, 1000 nM) were added to the medium on the first day of culture, and the medium was changed to normal medium from the second day of culture and continue the culture for 3 days, and then the ovaries were collected; the control group was incubated with 50 ng/ml folliculopoietin FSH (Sigma #F4021-2UG). The collected ovaries were sectioned and stained to observe the morphology, and the results are shown in FIG. 1A (arrows point to primary follicles). FIG. 1B shows the results of counting follicles of all levels in the ovarian tissue of different treatment groups. The results demonstrated that the number of primordial follicles and early primary follicles was significantly increased in ovaries treated with VCD compared with those of the control group. FIG. 1C shows that ovaries of PD2 mice were treated with 10 nM VCD for 3 min in vitro before tissue proteins were collected, and the changes in the levels of protein phosphorylation associated with follicle activation in the ovaries were observed by Western blotting assay. The results showed that VCD treatment for 2-3 min could significantly activate the PI3K-Akt pathway, in which the expression of the involved proteins was significantly elevated. It can be seen that low concentration of VCD treatment stimulated the activation of primordial follicles.

Figure 2:
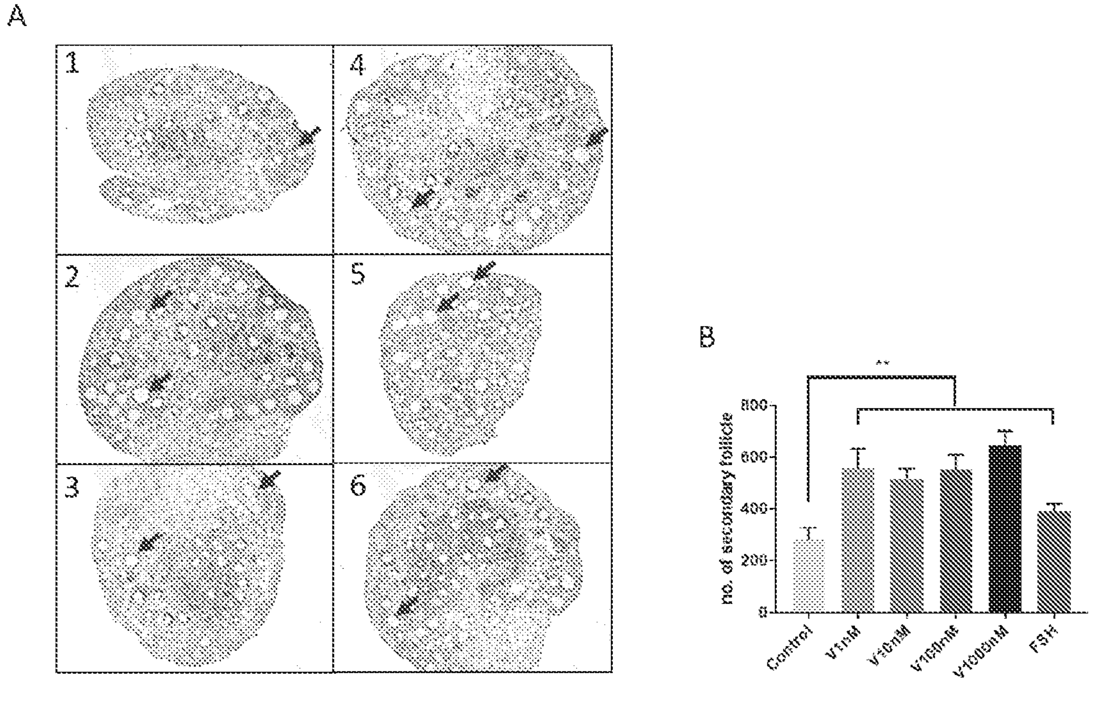
FIG. 2 shows that short VCD culture duration stimulates the transformation of primordial follicles to primary follicles in in vitro experiments.

Example 3 Short Duration VCD Culture Stimulates the Transformation of Primordial Follicles to Primary Follicles in In Vitro Experiments Mouse ovaries at 12 days (PD12) were isolated and cultured in vitro according to the method described in Example 1. Ovaries were collected after 4 days of incubation with different concentrations of 4-vinylcyclohexene diepoxide (VCD) (0, 1 nM, 10 nM, 100 nM, 1000 nM) in the medium, and 50 ng/ml of folliculopoietin FSH (Sigma #F4021-2UG) in the medium for the control group, in each group of mice N=9. The collected ovaries were sectioned and stained to observe the morphology. The results are shown in FIG. 2A (arrows point to normal secondary follicles). FIG. 2B shows the results of counting secondary follicles in ovarian tissues of different treatment groups. The results demonstrate that the number of secondary follicles in the ovaries treated with VCD was significantly increased compared to the control group.

Figure 3:
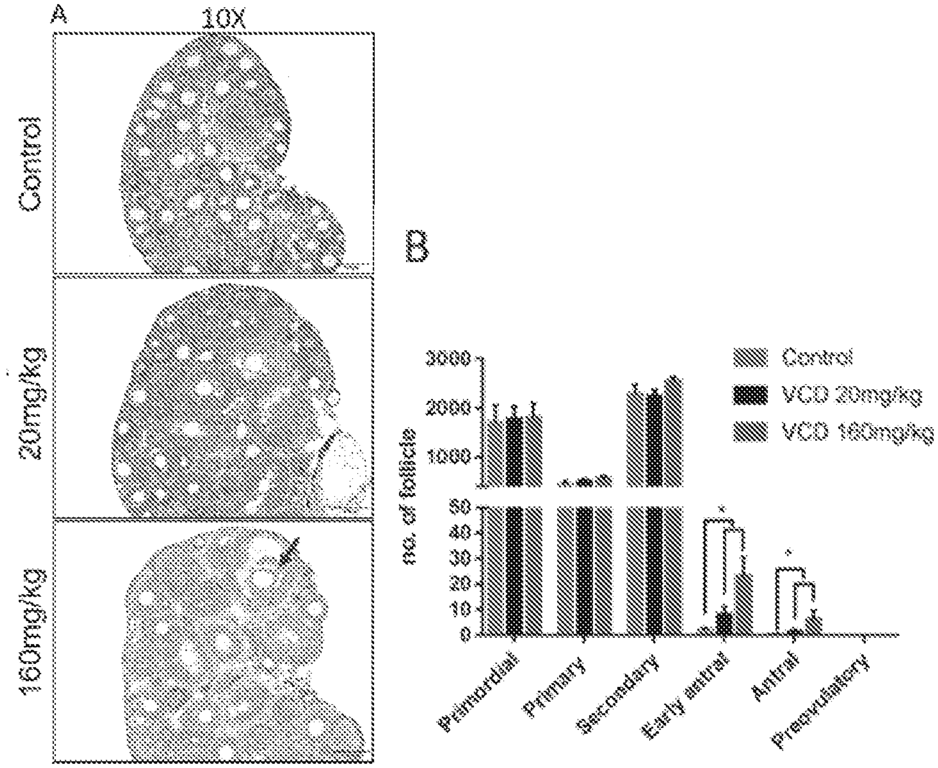
FIG. 3 shows that VCD stimulates follicle development in neonatal mice in vivo experiments.

Example 4 VCD Stimulates Follicle Development in Neonatal Mice In Vivo Experiments According to the method described in Example 1, the same litter of PD12 C57bl/6 female mice was divided into experimental and control groups according to body weight and given 20 mg/kg or 160 mg/kg of VCD by intraperitoneal injection, while the control mice were given the same volume of saline. Each group (N=6) was administered for 5 consecutive days, and then the mice were executed and the collected ovaries were stained to observe the morphology as shown in FIG. 3A (yellow arrows indicate early sinus follicles and red arrows indicate sinus follicles). FIG. 3B shows the results of follicle counts in ovarian tissues of different treatment groups after 5 days of continuous administration. The results demonstrate that there were more follicles close to the preovulatory stage in the ovaries of the mice in the administered group compared to the control group.

Together with the phenomena observed in Example 3, it can be concluded that VCD treatment can stimulate the transformation of primary and secondary follicles to mature oocytes.

Example 5 VCD Promotes Follicle Development as Well as More Mature Oocytes Expulsion in an In Vivo Experiment in Old-Aged Mice Aged mice of 10-12 months were used as study subjects to observe the effect of VCD on follicle development and eventual oocytes expulsion in their ovaries.

Figure 4:
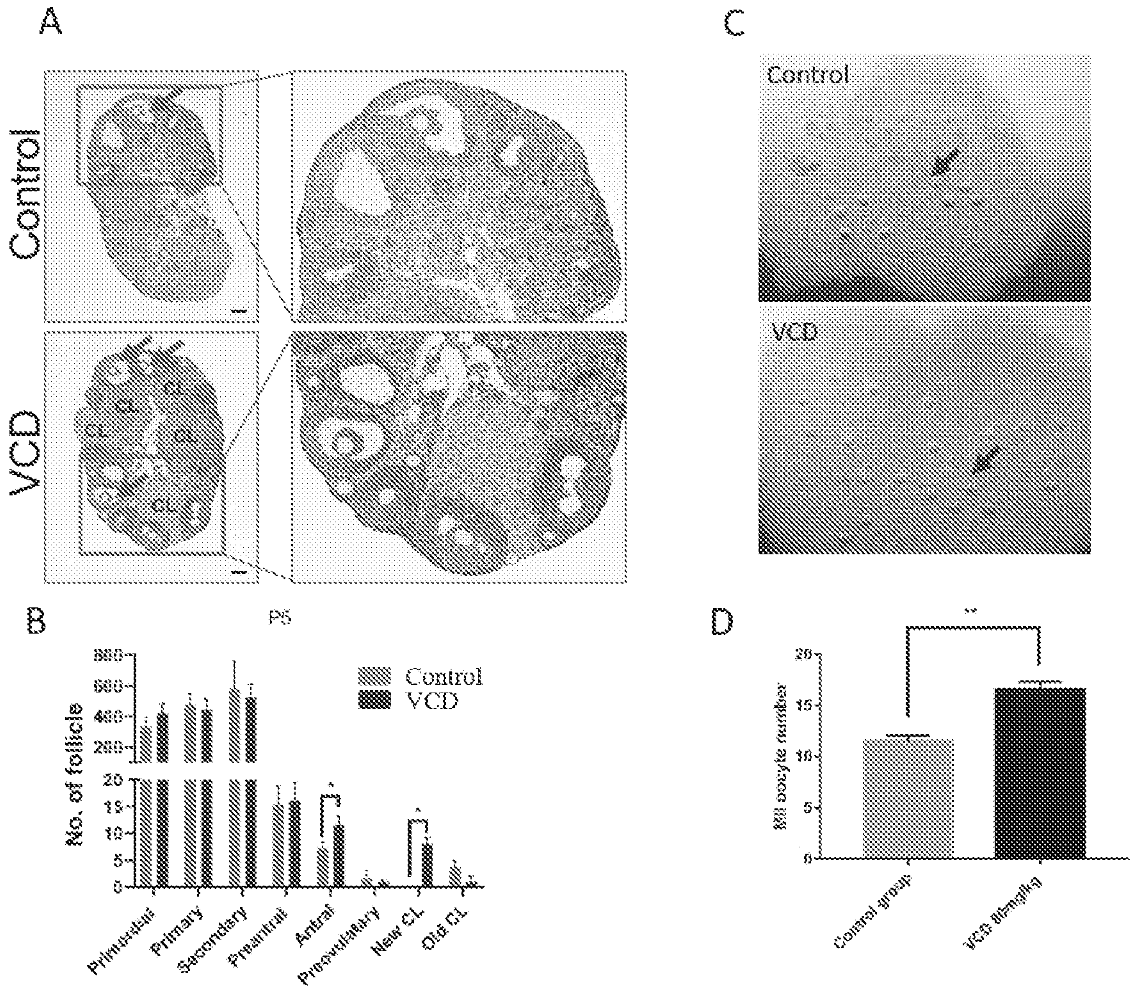
FIG. 4 shows that VCD stimulates follicle development as well as more oocytes expulsion in the in vivo experiments in old mice.

According to the method described in Example 1, 10-12 month old C57bl/6 rats were divided into experimental and control groups according to their body weight, and the experimental group was weighed and injected intraperitoneally with 80 mg/kg of VCD, while the control group was given the same volume of saline. After 5 days of administration, 5 units of PMSG were injected into the experimental animals, and then 10 IU of hCG was injected 48 hours later to induce secondary ovulation. 16 hours after the hCG injection, the mice were executed, and the MII oocytes were collected from the oviducts of both sides. The collected ovaries were sectioned and stained to observe the morphology, and the results are shown in FIG. 4A (arrows point to preovulatory follicles, CL refers to corpus luteum). FIG. 4B shows the results of counting different follicles in the ovarian tissues of different treatment groups. The results of follicle counts indicate that there were more sinus follicles as well as newly formed corpus luteum in the ovaries of mice given VCD. FIG. 4C shows the MII oocytes obtained by ovulation (arrows point to MII eggs). FIG. 4D shows the results of MII egg counts in the experimental and control groups. The ovulation results showed that the mice in the VCD group could ovulate more oocytes after 5 days of administration. It can be seen that VCD can improve ovarian function and further stimulate oocyte expulsion in aged mice.

Example 6 VCD Promotes the Expression of Aromatase in Ovarian Granulosa Cells and Estrogen Production Primary granulosa cells from PD20 mice were extracted and the effect of VCD treatment on the expression of aromatase in granulosa cells was observed.

Figure 5:
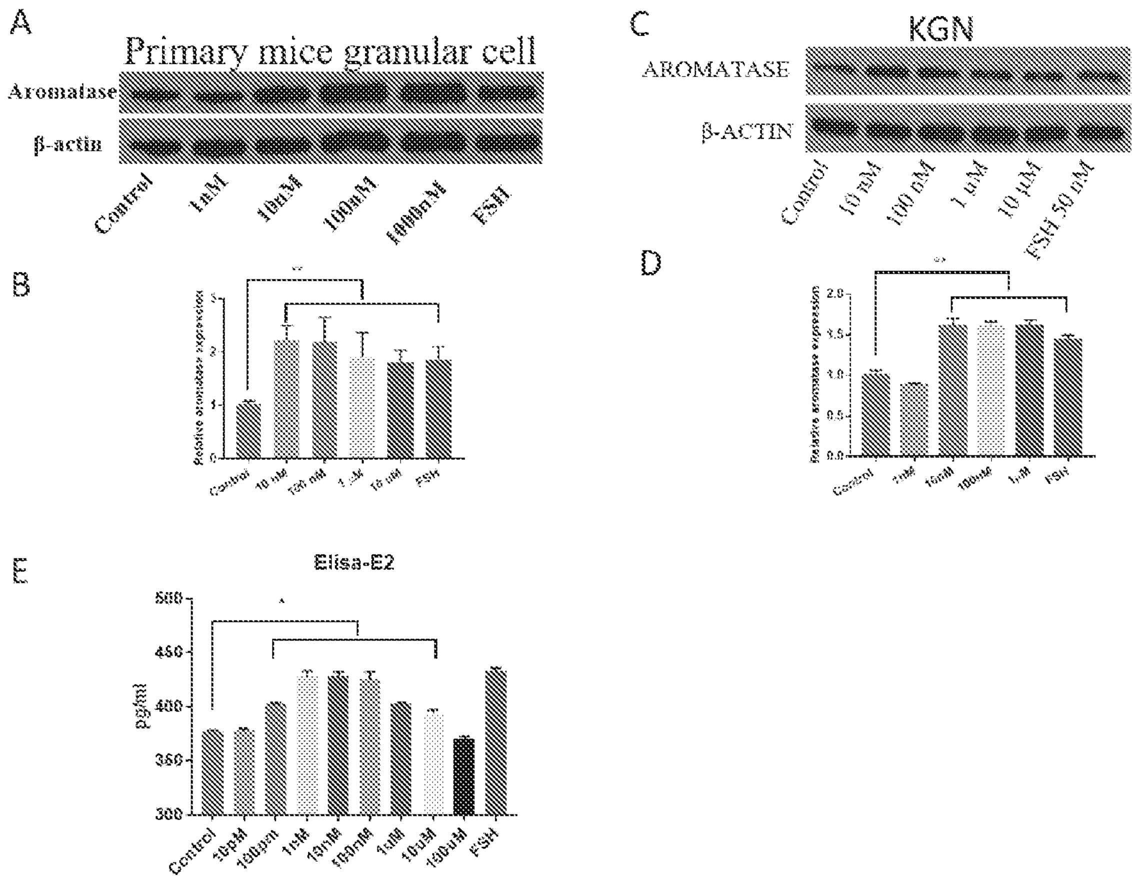
FIG. 5 shows that VCD stimulates aromatase expression and estrogen production in ovarian granulosa cells.

Granulosa cells were isolated from the ovaries of PD20 mice according to the method described by Reddy P et al, Science 2008, 319(5863):611-613 and Liu Y X et al Biol Reprod 1986, 35(1):27-36, from which primary granulosa cell lines were obtained. They were treated with different concentrations of VCD (0, 1 nM, 10 nM, 100 nM, 1000 nM) for 24 h, using 50 ng/ml FSH as control. The results showed that the expression level of aromatase in mouse granulosa cells was significantly increased after VCD treatment (FIG. 5A-B)

Human-derived granulocyte-like cell line KGN (provided by Prof. Toshihiko Yanase, Fukuoka University, Japan) was cultured in DMEM/F12 medium. KGN were treated with different concentrations of VCD (0, 1 nM, 10 nM, 100 nM, 1000 nM) for 24 h, using 50 ng/ml FSH as control. The results showed that the expression level of aromatase in KGN was significantly increased after VCD treatment (FIG. 5C-D). The production of estrogen (E2) in KGN culture supernatant was further observed by ELISA, and it was found that the level of estrogen in the cell supernatant of VCD-treated group was significantly higher than that of the control group (FIG. 5E).

The above data suggest that VCD has a role in promoting the expression of granulocyte aromatase and its downstream estrogen production.

The inventors of the present invention discover for the first time that VCD apparently exhibits both dose- and duration-dependent opposing, hormone-like effects on the maintenance of primordial follicle pool, follicle development, and ovulation induction. This effect of VCD is due to that low concentration and/or short duration treatment with 4-vinylcyclohexene diepoxide has hormone-like effects on ovary or cultured ovarian tissue, and can transiently activate PI3K-akt and mTOR pathways; in addition, low concentration and/or short-term 4-vinylcyclohexene diepoxide treatment also increases expression of aromatase in ovarian granulosa cells stimulates estrogen production. The present invention thus provides a method and a culture medium for treating mammalian ovaries including human ovaries in vivo, or culturing isolated ovaries or ovarian tissues in vitro with 4-vinylcyclohexene diepoxide.

The foregoing is a description of the present invention and is not to be regarded as a limitation of the invention. Unless otherwise indicated, the present invention will be practiced using conventional techniques of organic chemistry, polymer chemistry, biotechnology, etc., and it is clear that the invention can be achieved in other ways than those described specifically in the above description and embodiments. Other aspects and improvements within the scope of the present invention will be apparent to those skilled in the art to which the present invention belongs. Many changes and variations are feasible in accordance with the teachings of the present invention and are therefore within the scope of the present invention.

The invention claimed is:

1. An in vitro culture method of ovary or ovarian tissue of a mammal, said method comprising adding 4-vinylcyclohexene diepoxide or its analog in a culture medium, wherein the 4-vinylcyclohexene diepoxide is about 1.0 nM-20 nM in the culture medium.

2. The in vitro culture method according to claim 1, wherein the time for the ovary or ovarian tissue being cultured in the culture medium with 4-vinylcyclohexene diepoxide is no more than 6 days.

3. The in vitro culture method according to claim 1, which is used to treat the ovary or ovarian tissue of juvenile or young mammals, and the time for the ovary or ovarian tissue being cultured in the culture medium with 4-vinylcyclohexene diepoxide is not more than 4 days.

4. The in vitro culture method according to claim 1, which is used to treat the ovary or ovarian tissue of middle-aged or old mammals, and the time for the ovary or ovarian tissue being cultured in the culture medium with 4-vinylcyclohexene diepoxide is not more than 6 days.

5. The in vitro culture method according to claim 2, wherein the time for the ovary or ovarian tissue being cultured in the culture medium with 4-vinylcyclohexene diepoxide is no more than 1 day.

* * * * *